United States Patent [19]

Zweig et al.

[11] 4,202,323
[45] May 13, 1980

[54] DRUG ACTIVATION BY RADIATION

[76] Inventors: Jack Zweig, 145 Vaneck Dr., New Rochelle, N.Y. 10804; William McLaughlin, 3901 Albemarle St., NW., Washington, D.C. 20016; Matthew L. Herz, 20 Swanson Rd., Framingham, Mass. 01701

[21] Appl. No.: 900,897

[22] Filed: Apr. 28, 1978

[51] Int. Cl.² .................... A61K 29/00; A61B 10/00
[52] U.S. Cl. ................................... 128/1.1; 424/1; 424/1.5; 424/2; 424/9
[58] Field of Search ................ 424/1, 1.5, 2, 9; 128/1 R, 1.1, 172.1

[56] References Cited

U.S. PATENT DOCUMENTS 4,106,488   8/1978   Gordon ........................... 424/1

*Primary Examiner*—Benjamin R. Padgett
*Assistant Examiner*—Christine M. Nucker
*Attorney, Agent, or Firm*—Howard C. Miskin

[57] ABSTRACT

A method of selectively causing drug activation within a living body which comprises administering to a living body a polyamino arylmethylnitrile capable of undergoing controlled cleavage to form a polyaminoaryl methyl ion and/or a free cyanide ion, the drug also being soluble in the body serum so that it is capable of passing via oral, intramuscular or intra-peritoneal administration into a body, and then subjecting a localized area of said body to radiation capable of causing cleavage of the cyanide ion from the drug precursor, the resulting ions acting to sensitize the localized area to radiation.

12 Claims, 1 Drawing Figure

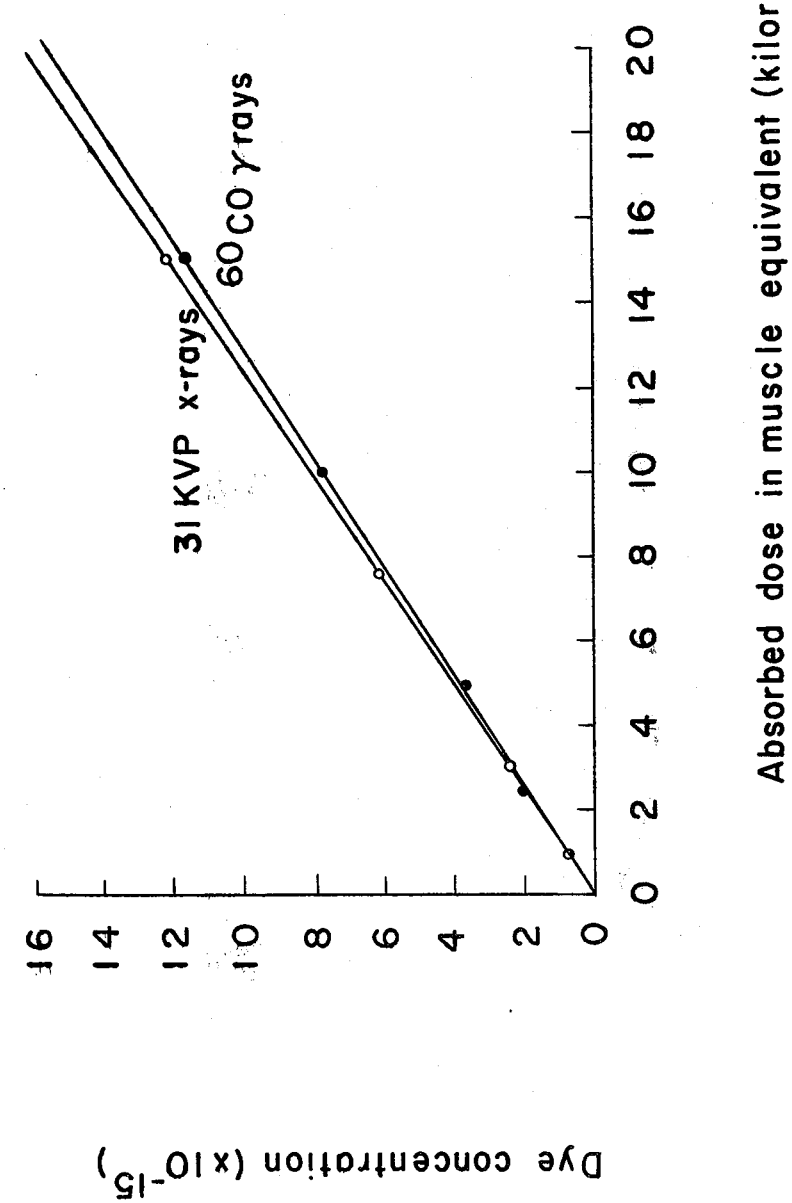

DRUG ACTIVATION BY RADIATION

BACKGROUND OF THE INVENTION

(1) Field of the Invention

This invention relates to the in-viva activation of materials to produce drugs which act as an antitumor agent and particularly is concerned with polyarylacetonitrile compositions which upon irradiation release cyanide ion and dye to act against tumor cells. Thus, the administration of selected materials to patients with localized neoplastic disease followed by localized exposure to ionizing radiation as contemplated by this invention is operable to cleave the molecule, splitting off active species which can then act synergistically with the radiation to destroy tumor cells.

(2) Description of the Prior Art

Ionizing radiation is one of the most effective modalities for the treatment and cure of certain localized malignant tumors. In general, radiation therapy is most effective against tumors having a high percentage of cells that are undergoing cell division at the time of treatment. Studies done to determine the cause of cell death secondary to gamma irradiation indicate that the mechanism primarily involves oxidation and ionization leading to lethal free radical formation during the reproductive phase of the cell cycle.

It would be beneficial to introduce some substance into the body which would then be distributed throughout the tissues including the tumor, without causing ill effects, and which upon irradiation of the tumor locally, would break down to yield a highly reactive end product, either a free radical, a reactive ion or a reactive molecule to potentiate the effect of the irradiation. That is to say that this radiation or photolysis product would be expected to remain localized in the tumor to contribute to the death of the tumor cells, thereby increasing the scope of ionizing radiation and freeing the radiation therapist from the confines of treating only those tumors with a large fraction of the cells undergoing cell division. It would also be expected to reduce the magnitude of the radiation dose necessary to cause tumor regression and cell destruction, thereby diminishing radiation damage to surrounding healthy tissue.

SUMMARY OF THE INVENTION

It is, therefore, among one of the principal objectives of this invention to provide a method of activating a drug by photolysis or radiolysis after it has been localized in a neoplastic area to contribute to the death of the tumor cells in that area.

In accord with the invention, there has been discovered a method of selectively causing drug activation in a localized area within a living body which comprises administering to said body a polyarylacetonitrile capable of undergoing cleavage to form a polyaryl methyl ion and/or molecule and a free cyanide ion, said nitrile also being soluble in the body serum so that it is capable of passing via oral administration or by injection into a localized area of the body, and then subjecting said localized area to radiation capable of causing cleavage to cyanide ion and carbocation in said localized area, said cyanide ion and/or carbocation acting as a radiation sensitizer(s) in said localized area.

DESCRIPTION OF THE PREFERRED EMBODIMENTS

A number of electron-affinic compounds, such as nitroimidazole or metronidazole are known to radiation-sensitize hypoxic tumor cells. The present invention deals with substituted aminotriarylacetonitriles. It has long been known that certain of these compounds, upon absorption of energy, release cyanide ion and a residual molecular component. The resulting amino substituted triaryl methylene dye formed by heterolytic cleavage of the cyanide ion is stable against radiation initiated degradation and is unreactive in aqueous media. It is solubilized, readily dispersed in tissue, and binds covalently with DNA, RNA and proteins, yet is not a known carcinogen as are many aryl and alkyl amines, halogenated hydrocarbons and certain reactive cyclic compounds. Moreover, instantaneous staining of tissue by the dye acts as an indicator for cyanide distribution. Weakly amphoteric triarylmethane dyes which are substituted with sulfonic acid salts, hydroxy groups, and other solubilizing groups have been used safely for coloring drugs, cosmetic and foods and are not considered carcinogenic. In fact, certain related nitrogen-bridged substituted compounds, e.g. acridine orange and auramine, have been used themselves to retard tumor cell growth.

In a recent study, tissues which were radio-sensitive were found to have, during irradiation, the free radical semihyroascorbate, which was not present in radio-resistant tissue.

Cell death would occur if molecules formed from the interaction of the radiation and the molecular contents of the cell having the ability to:

1. Inhibit enzyme action completely via denaturation or specific binding of an inhibitor to the enzyme.
2. Destroy the integrity of the cell membrane.
3. Activate the lysozymal enzymes with the cell, or
4. Destroy the integrity of DNA beyond repair.

Experimental evidence indicates that DNA destruction, mediated by free radical formation during the period of irradiation, is probably the primary cause of cell death secondary to ionizing radiation.

It was observed many years ago that oxygenation of certain tissue prior to exposure to ionizing irradiation leads to an increased destruction of cells. Oxygen enhancement of cell killing depends on many factors (oxygen concentration, period of oxygenation, radiation quality, culture conditions of cells, genetic background, etc.). Therefore, it is possible to introduce into the cells of a tumor a radiation-sensitive compound. Radiolysis of this compound would yield an end product reactive enough to destroy that which otherwise would be radiation-insensitive tissue. The compound would have to have the following properties:

1. Be relatively non-toxic and stable when given systemically.
2. Be able to enter and remain in the cell.
3. Be rapidly cleared from the blood stream.
4. Break down upon gamma irradiation to yield highly reactive end products. These products would bind with key portions of enzymes necessary for life, thereby inhibiting their action; or alternatively, they would bind to the DNA, destroying the usefulness of the deoxyribonucleic acids in cell reproduction and enzyme synthesis.

Any substantially colorless radiation reactive organic nitriles which are non-toxic and which produce cyanide ion when irradiated as the primary radiation product may be used to augment the therapeutic effects of radiation. Examples of such nitriles and derivatives which may be cited to illustrate but not to limit the invention include compounds from the class consistency of (1) amino substituted triphenylmethane dye leuconitriles, (2) arythromycin leuconitrile derivatives, (3) amino substituted triarylmethyl dye leuconitriles, and nitriles of adriamycin and its analogs.

The invention will be further illustrated in conjunction with the following specific example which is not to be considered as limiting the invention thereto.

The leuconitrile disodium salt of 4-diethylaminophenyl-4'4''-bis-(3-sulfobenzylethylaminophenyl)acetonitrile was prepared by standard technique, such as that disclosed in U.S. Pat. No. 2,839,543 (L. Chalkley). The compound was thermoset into a gel, muscle-equivalent consisting primarily of polyvinylpyrrolidone and polyvinyl chloride. It was irradiated with various doses of $60_{Co}$ gamma rays and diagnositc x-rays (31 kVp), in order to determine the degree of linearity of the dye and cyanide production. (see FIG. 1).

Twenty gram female mice in groups of three were then injected intraperitoneally with a solution of 10 mg/cc and a suspension of 32 mg/cc of the nitrile in normal saline. 0.1 ml, 0.2 m. and 0.3 ml doses were administered. There were a total of six groups of mice with each mouse receiving only one injection. An additional control group was injected with 0.3 ml of normal saline. The mice were then observed for two weeks.

After observation for more than two weeks none of the animals given the compound succumbed. The animals which had been sacrificed and irradiated appeared to have absorbed the compound since no particulate matter could be found. Upon irradiation the peritoneum turned light blue due to the presence of dye produced by the radiation induced cleavage. The cut skinned surface of the sacrificed mice after uv irradiation became blue in color, demonstrating that the compound had been absorbed and dispersed throughout the tissue, and that the desired cleavage could be effected by radiation.

Three additional mice were injected with the suspension and after six hours were sacrificed. The abdomen was opened and the peritoneal contents exposed to ultraviolet radiation with a wavelength of 253.7 nm. Another group of animals were injected with 0.3 cc of the suspension, then sacrificed after 6 hours and skinned. The cut surface was then irradiated as before to induce dye formation.

The linearity of dye formation in the muscle-equivalent gel with gamma-ray and x-ray dose is shown in the accompanying figure. From these results, i.e. a linear relationship with a zero intercept, it can be seen that there was no threshold for the release of cyanide upon irradiation.

These mice were administered a dose of the compound in solution equivalent to 160 mg/kg. The solution and suspension were stored in dark bottles. The suspension was administered in amounts equivalent to 480 mg/kg.

The $LD_{50}$ of $CN^-$ is about 0.5 mg/kg. The molecular weight of this leuconitrile compound is 789. Cyanide accounts for 3.3% of the molecular weight. Therefore, 5 mg and 15 mg per kilogram of cyanide was introduced into the animals without causing death. The cyanide functionality remained bound in the compound until induced cleavage occurred, and only then was the free cyanide moiety released. Thus it is possible to administer high doses of the cyanide-containing compound to living tissue and then selectively release cyanide ion with localized irradiation.

Partially water soluble, non-toxic substituted aminopoly arylacetonitriles of this type are ideal for the purpose of in situ controlled cyanide ion generation. In accord with the invention in-vitro and in-vivo tests leave determined that:

1. Compounds of this type release cyanide linearly with photon irradiation.
2. These substances can be administered in large doses without killing the animal.
3. The compounds similar to the example can be localized and remain intact within the tissue prior to irradiation.
4. The compounds break down upon photon irradiation after administration to the animal to yield the active cyanide ion. The appearance of a color following irradiation indicates that the cyanide ion is cleaved and is free to react with tumor tissue.

It should be noted that simple forms of dye precursor, namely substituted aminotriphenylacetonitriles have been used in acidic aqueous or organic solutions to determine accurately radiation absorbed dose by means of spectrophotometric measurement of color intensity.

The material employed in the foregoing example is a member of a group of compounds that may yield many substances with all of the above properties or with improved properties. Structurally, compounds of this class consist of a cyanide moiety bound to a methane which is substituted with three hydrogens replaced by aniline groups.

The compound itself is relatively stable against radiolytic scission of all bonds except the

bond. Irradiation at body temperature causes immediate heterolysis with dye formation and release of cyanide ion. Energy losses due to fluorescence are not significant. What is more, we have verified that the release of cyanide by irradiation of the polyarylacetonitrile is proportional to radiation dose with a yield of about $2 \times 10^{10}$ cyanide ions per erg of radiation energy absorbed by a 10 mmol aqueous solution of the compound. For a radiation dose of 50 rads, this corresponds to about $10^{14}$ ions per gram of tissue, or about 1 mmol of cyanide ion.

The cyanide ion complexes with most of the transitional metals such as Zn, Cu, Ni, Fe. It complexes readily with the ferric ion in biologic systems which leads to inactivation of the cytochrome system, necessary for transport across the cell membrane and electron transport for aerobic glycolysis. Most enzymes contain heavy metals of the transitional group. Thus far, transitional metals have been identified in 27% of all the enzymes. These metals appear to be necessary for the activity of the enzyme. Thus, the anticipated metal complexing with cyanide could lead to either inactivation or augmentation of enzyme activity. Rat brain slices when incubated with cyanide for 40 minutes show irreversible damage with disorganization of cellular oranelles, such as the rough surfaced endoplasmic reticulum, mitochondria, and polysomes. In addition cyanide ion has been shown to potentiate x-ray sensitivity in various tissues.

Inactivation of cyanide ion in man occurs primarily by formation of relatively nontoxic thiocyanate ion via the action of the enzyme Rhodanese which is present in most cells. For this reason the ability of cyanide to function as a localized tumoricidal agent would be dependent upon its ability to be liberated in high enough concentrations so as to override the action of Rhodanese locally. In addition, normal tissue exposed to radiation would also be poisoned by the released cyanide; therefore, the reaction would have to remain localized with a minimum of spillage in the general circulation.

In summary, by combining drug and radiation treatment of cancer the effectiveness of treatment can be synergystically improved. The improvements result mainly from increase in cell mortality due to:

1. Deactivation of enzymes through the introduction of radiolytic products as selective radical anion probes.
2. Radiation-initiated binding of lethal covalent adducts to DNA. The present invention offers a new approach to these ends.

We have shown that a certain aminotriarylacetonitrile is non-toxic when administered in large doses to mice and releases free cyanide ion linearly with absorbed dose of short-wave ultraviolet or ionizing radiation. Since the cyanide ion is readily complexed with certain transition metals ($Fe^{+++}$, $Co^{+++}$ etc.), the radiolytic reaction at the physiological pH would be expected to form species toxic to cells in an irreversible manner. Staining of the irradiated region results due to dye formation from the acetonitrile. This dye binds readily to DNA, RNA, and proteins, but is non-toxic and non-carcinogenic.

Thus, the foregoing disclosure gives evidence that triarymethane leuconitrile compounds are able to enter and remain in living tissue until induced cleavage forms dye and cyanide ions. These materials have been shown to undergo predictable chemistry to a degree linearly dependent on the amount of radiation. These facts indicate a class of materials which would be efficacious in the treatment of cancer in conjunction with radiation. At the outset they possess the ability to introduce an inert agent to a site at which radiation will produce a measured amount of an active agent for selective cell destruction.

In a tumor where the leuconitrile would permeate and where the largest energy deposition would occur due to treatment-planned irradiation, cyanide ion as a product of radiolysis may act in at least three ways to induce regression of tumor cells. As a selective radical-ion probe, it can:

1. Increase electron-affinic radiosensitivity of hypoxic cells.
2. Catalyze radiolytic deactivation of enzymes.
3. Complex with transition metals and inhibit enzyme activity, thus contributing to cell death.

A balance would have to be sought in selecting the optimum dose of the nitrile prior to irradiaion. The transitory $(CN)_2^-$, $(SCN)_2^-$, and $CN^-$ concentrations in the tumor after radiation treatment should be great enough to offset deactivation by $SCN^-$ formation, which outside the periphery of the tumor would be expected to ameliorate toxicity of healthy tissue.

While there has been described and illustrated a preferred embodiment of the present invention, it is apparent that numerous alterations, omissions and additions may be made without departure from the spirit thereof.

What is claimed is:

1. A method of selectively causing drug activation in a localized area within a living body which comprises administering to said body a substituted aminotriarylacetonitrile capable of undergoing radiation induced cleavage to form a substituted aminotriarylmethyl component and a free cyanide component, said nitrile being soluble in the body serum so that it is capable of passing by the administration thereof to said body, and then subjecting a localized area to radiation capable of causing cleavage of said cyanide species from said nitrile in said localized area, said cyanide ion and/or carbocation acting as a radiation sensitizer in said localized area.

2. A method according to claim 1, wherein said aminotriarylacetonitrile is substituted with one or more sulfonic acid or sulfonate groups.

3. A method according to claim 1, wherein said aminotriarylacetonitrile is the disodium salt of 4-diethylaminophenyl-4',4''-bis-(3-sulfobenzylethylaminophenyl)acetonitrile.

4. A method according to claim 1, wherein the substituted aminotriarylacetonitrile is hydrophilic.

5. A method according to claim 1, wherein said radiation is gamma irradiation.

6. A method according to claim 1, wherein said radiation is x-ray irradiation.

7. A method according to claim 1, wherein said radiation is ultraviolet irradiation.

8. A method according to claim 1, wherein said localized area is neoplastic.

9. A method according to claim 1, wherein said administration is oral.

10. A method according to claim 1, wherein said administration is by injection.

11. A method according to claim 10, wherein said injection is given intra-peritoneally.

12. A method according to claim 3, wherein up to 15 mg/kilo of cyanide was administered to said body in the form of said disodium salt.

* * * * *